US007452973B2

(12) United States Patent
Raines et al.

(10) Patent No.: US 7,452,973 B2
(45) Date of Patent: Nov. 18, 2008

(54) CELL-PERMEABLE FLUORESCENT PROTEINS

(75) Inventors: Ronald T. Raines, Madison, WI (US); Stephen M. Fuchs, Carrboro, NC (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/593,664

(22) Filed: Nov. 7, 2006

(65) Prior Publication Data

US 2007/0105182 A1 May 10, 2007

Related U.S. Application Data

(60) Provisional application No. 60/734,210, filed on Nov. 7, 2005.

(51) Int. Cl.
*C07K 14/00* (2006.01)
*C12N 15/12* (2006.01)
*C12N 15/63* (2006.01)
*C07H 21/04* (2006.01)

(52) U.S. Cl. .................... 530/350; 435/69.1; 435/69.7; 536/23.5

(58) Field of Classification Search ................. 530/350; 435/69.1, 69.7; 536/23.5
See application file for complete search history.

(56) References Cited

U.S. PATENT DOCUMENTS

| | | | |
|---|---|---|---|
| 5,777,079 | A | 7/1998 | Tsien et al. |
| 6,469,154 | B1 | 10/2002 | Tsien et al. |
| 6,638,732 | B1 | 10/2003 | Evans |

OTHER PUBLICATIONS

Cody, C.W., et al., "Chemical Structure of the Hexapeptide Chromophore of the Aequorea Green-Fluorescent Protein," Biochemistry 32:1212-1218 (1993).

Cormack, B.P., et al., "FACS-optimized mutants of the green fluorescent protein (GFP)," Gene 173:33-3 (1996).

Fuchs, S.M., et al., "Pathway for Polyarginine Entry into Mammalian Cells," Biochemistry 43:2438-2444 (2004).

Fuchs, S.M., et al, "Visions & Reflections, Internalization of cationic peptides: the road less (or more?) traveled," Cell. Mol. Life Sci. 63:1819-1822 (2006).

Fuchs, S.M., et al., "Polyarginine as a multifunctional fusion tag," Protein Science 14:1538-1544 (2005).

Hanson, G.T., et al., "Green Fluorescent Protein Variants as Ratiometric Dual Emission pH Sensors. 1. Structural . . . ," Biochemistry 41:15477-15488 (2002).

Hanson, G.T., et al., "Investigating Mitrochondrial Redox Potential with Redox-sensitive Green Fluorescent . . . ," The Journal of Biological Chemistry 279:13044-13053 (2004).

Hoffman, R.M., "The Multiple Uses of Fluorescent Proteins to Visualize Cancer in vivo," Nature 5:796-806 (2005).

Marafino, B.J., Jr., et al., "Commercial Development Considerations for Biotechnology-Derive Therapeutics," Cardiovascular Toxicology 03:5-12 (2003).

Pace, C.N., et al., "Charge-charge interactions influence the denatured state ensemble and contribute to protein stability," Protein science 9:1395-1398 (2000).

Richard, J.P., et al., "Cellular Uptake of Unconjugated TAT Peptide Involves Clathrin-dependent Endocytosis and Heparan . . . ," The Journal of Biological Chemistry 280:15300-15306 (2005).

Rosenow, M.A., et al., "The Crystal Structure of the Y66L Variant of Green Fluorescent Protein Supports a Cyclization-Oxidation-Dehydration Mechanism . . . ," Biochemistry 43:4464-4472 (2004).

Stepanenko, O.V., et al., "Comparative Studies on the Structure and Stability of Fluorescent Proteins EGFP, zFP506, mRFP1, "dimer2", and DsRed1," Biochemistry 43:14913-14923 (2004).

Waldo, G.S., et al., "Rapid protein-folding assay using green fluorescent protein," Nature Biotechnology 17:691-695 (1999).

Warf, T.H., "The Uses of Green Fluorescent Protein in Mammalian Cells," Green Fluorescent Protein: Properties, Applications, and Protocols, Second Edition 305-337 (2006).

Zacharias, D.A., "Molecular Biology and Mutation of Green Fluorescent Protein," Green Fluorescent Protein: Properties, Applications, and Protocols, Second Edition 83-120 (2006).

*Primary Examiner*—Chih-Min Kam
(74) *Attorney, Agent, or Firm*—Quarles & Brady LLP

(57) ABSTRACT

This invention relates to methods and compositions for designing novel fluorescent proteins, preferably to a green fluorescent proteins (GFP). The engineered GFPs are modified by substituting negatively charged amino acids with positively charged amino acids on the exterior of the protein making the protein cell permeable. The ability of the engineered fluorescent proteins to permeate cells obviates the need for transfections, allowing these novel proteins to be used in numerous biological applications.

13 Claims, 10 Drawing Sheets

```
     1          11         21         31         41          SEQ ID NO:
GFP  mskgeelftg vvpilvelDg dvnghkfsvs gegegdatyg kltlkfictt    1
BFP  mskgeelftg vvpilveldg dvnghkfsvs gegegdatyg kltlkfictt    2
YFP  mskgeelftg vvpilveldg dvnghkfsvs gegegdatyg kltlkfictt    3
CFP mvskgeelftg vvpilveldg dvnghkfsvs gegegdatyg kltlkfictt    4

    51         61         71         81         91
GFP gklpvpwptl vttfXXXvqc fsrypdhmkq hdffksampe gyvqertiff
BFP gklpvpwptl vttfXXXvqc fsrypdhmkr hdffksampe gyvqertiff
YFP gklpvpwptl vttfXXXlqc farypdhmkr hdffksampe gyvqertiff
CFP gklpvpwptl vttlXXXvqc fsrypdhmkq hdffksampe gyvqertiff

    101        111        121        131        141
GFP kddgnyktra evkfegdtlv nrielkgidf kedgnilghk leynynshnv
BFP kddgnyktra evkfegdtlv nrielkgidf kedgnilghk leynfnshnv
YFP kddgnyktra evkfegdtlv nrielkgidf kedgnilghk leynynsgnv
CFP kddgnyktra evkfegdtlv nrielkgidf kedgnilghk leynyishnv

    151        161        171        181        191
GFP yimadkqkng ikvnfkirhn iedgsvqlad hyqqntpigd gpvllpdnhy
BFP yimadkqkng ikvnfkirhn iedgsvqlad hyqqntpigd gpvllpdnhy
YFP yimadkqkng ikvnfkirhn iedgsvqlad hyqqntpigd gpvllpdnhy
CFP yitadkqkng ikanfkirhn iedgsvqlad hyqqntpigd gpvllpdnhy

    201        211        221        231
GFP lstqsalskd pnekrdhmvl lefvtaagit hgmdelyk
BFP lstqsalskd pnekrdhmvl lefvtaagit hgmdelyk
YFP lsyqsalskd pnekrdhmvl lefvtaagit hgmdelyk
CFP lsyqsalskd pnekrdhmvl lefvtaagit lgmdelyk
```

■ = acidic residue mutated to arginine
□ = basic residue possibly important for internalization
_ = alternative acidic (negative) residues that can be substituted
X = residues that constitute the chromophore

FIG 9

```
-58          -46
ATGCGGGGTTCTCATCATCATCATCATCATGGTATGGCTAGCATGACTGGTGGACAG SEQ ID NO:9
  1
CAAATGGGTCGGGATCTGTACGACGATGACGATAAGGATCCCCCCGCTGAATTCATG
55
AGTAAAGGAGAAGAACTTTTCACTGGAGTTGTCCCAATTCTTGTTCGTTTACGTGGT
112
CGTGTTAATGGGCACAAATTTTCTGTCAGTGGAGAGGGTGAAGGTGATGCAACATAC
169
GGAAAACTTACCCTTAAATTTATTTCCACTACTGGAAAACTACCTGTTCCATGGCCA
226
ACACTTGTCACTACTCTCACTTATGGTGTTCAATGCTTTTCAAGATACCCAGATCAT
283
ATGAAACGGCATGACTTTTTCAAGAGTGCCATGCCCGAAGGTTATGTACAGGAAAGA
340
ACTATATTTTTCAAAGATGACGGGAACTACAAGACACGTGCTCGTGTCAAGTTTGAA
397
GGTGATACCCTTGTTAATAGAATCCGTTTAAAAGGTATTGATTTTAAAGAAGATGGA
454
AACATTCTTGGACACAAATTGGAATACAACTATAACTCACACAATGTATACATCATG
511
GCAGACAAACAAAAGAATGGAATCAAAGTTAACTTCAAAATTAGACACAACATTGAA
568
GATGGAAGCGTTCAACTAGCAGACCATTATCAACAAAATACTCCAATTGGCGATGGC
625
CCTGTCCTTTTACCAGACAACCATTACCTGTCCACACAATCTGCCCTTTCGAAAGAT
682
CCCAACGAAAAGAGAGACCACATGGTCCTTCTTGAGTTTGTAACAGCTGCTGGGATT
739                            765
ACACATGGCATGGATGAACTATACAAATAA
```

ATG = translation start site
CATCATCATCATCATCAT = polyhistidine tag
ATG = GFP start site
= mutated residues
= basic residues important for internalization
= alternative residues for modification
TAA = translation stop codon

FIG 10

CELL-PERMEABLE FLUORESCENT PROTEINS

CROSS-REFERENCE TO RELATED APPLICATIONS

This application claims the benefit of U.S. Provisional Application No. 60/734,210 filed Nov. 7, 2005. The application is incorporated herein by reference in its entirety.

STATEMENT REGARDING FEDERALLY SPONSORED RESEARCH OR DEVELOPMENT

This invention was made with United States government support awarded by the following agency: NIH GM044783. The United States has certain rights in this invention.

BACKGROUND OF THE INVENTION

In biotechnology and genetic research, it is often desirable to use marker genes or proteins to test and experiment with genetic processes and gene expression methodologies. For example, if one seeks to test a gene transfection process, the first gene that is usually employed is a test gene the expression of which can easily be seen in the host. Thus, genes that encode colorimetric and fluorescent proteins have become popular tools for genetic and gene expression research.

One of the popular fluorescent markers that is used in this fashion is the green fluorescent protein (GFP). The GFP protein, originally isolated from the jellyfish *Aequorea*, absorbs light in the visible spectrum and fluoresces in a visible green shade. It has been found that the GFP protein can be expressed in many different hosts and organisms while still retaining the characteristic fluorescent activity. One common use of GFP is to place the GFP gene in tandem with some other gene so that the fluorescence of treated cells will indicate the presence and expression of transferred DNA.

The GFP protein is a robust and stable molecule. It forms a barrel-shaped tertiary structure with a series of beta sheets forming a stable cylinder with the three amino acid chromophore region formed in its interior. The exterior surface of the barrel shape of the proteins is natively anionic, but exhibits a mixture of charged residues to its environment.

Since GFP has been in use as a research tool, many variants of GFP have been developed for a variety of purposes. However, most of the work on the GFP molecule has been on the fluorescent region of the protein to change the spectral characteristics of the fluorescence or to enhance the amplitude of the fluorescence. The characteristic of cell permeability is not usually considered with regard to fluorescent proteins like GFP. Indeed, breaching the plasma membrane barrier is a limiting factor in the development of proteins and other biomolecules as therapeutics and diagnostic tools. (See Marafino, B. J., Jr. & Pugsley, M. K. *Cardiovasc. Toxicol.* 3, 5-12 (2003)). Accordingly, there is much interest in developing new means to deliver proteins and other macromolecules into cells.

BRIEF SUMMARY OF THE INVENTION

The present invention is summarized as relating to an engineered fluorescent protein, suitably green fluorescent protein (GFP) which is modified by replacing amino acids having negatively charged side chains with amino acids having positively charged side chains on the exterior of the protein making the protein cell permeable. The ability of the engineered fluorescent proteins to permeate cells obviates the need for transfections, allowing these novel proteins to be used in numerous biological applications.

In one aspect, the engineered fluorescent protein includes a GFP in which at least one residue with negatively charged side chains in the amino acid sequence of a native or an enhanced GFP is substituted with a residue having positively charged side chains. A suitable substitution may occur at any one of amino acid residue positions 17, 19, 21, 111, or 124 in the GFP, rendering the protein permeable to cells in culture.

Alternatively, the engineered fluorescent protein includes a GFP in which at least three residues with negatively charged side chains in the amino acid sequence of a native or an enhanced green fluorescent protein are substituted with residues having positively charged side chains. Suitable substitutions occur at amino acid residue positions 17, 19, and 21, rendering the protein permeable to cells in culture.

In a related aspect, the engineered fluorescent protein includes a GFP in which at least three residues with negatively charged side chains in the amino acid sequence of a native or an enhanced GFP are substituted with residues having positively charged side chains. Suitable substitutions occur at amino acid residue positions 17, 19, 21, 111, and 124, rendering the protein permeable to cells in culture.

In another aspect, the engineered form of GFP has at least three amino acid residues with negatively charged side chains, such as glutamic acid or aspartic acid, in the sequence of the native protein substituted by residues having positively charged side chains, such as arginine or lysine. The modified GFP is cell permeable (cpGFP).

One example of a cpGFP includes three negative amino acid residues substituted with residues having positively charged side chains, such as E17R, D19R, and D21R, substitutions (SEQ ID NO: 6).

Another example of a cpGFP includes five negative amino acid residues with residues having positively charged side chains, such as E17R, D19R, D21R, E111R, and E124R substitutions (SEQ ID NO: 7).

Another related aspect includes methods for producing the engineered fluorescent proteins. The method includes culturing host cells containing a nucleic acid molecule encoding an engineered GFP under conditions favoring the production of a cpGFP and isolating the cpGFP from the host cell.

A related aspect includes an isolated polynucleotide sequence defined by SEQ ID NO:8 encoding the amino acid sequence of the engineered form of GFP with E17R, D19R, and D21R substitutions. A more suitable polynucleotide sequence defined by SEQ ID NO: 9 includes E17R, D19R, D21R, E111R, and E124R substitutions.

In another aspect the invention includes further modifying the cpGFP to prepare a linker-modified cell permeable fluorescent protein. The linker-modified cell permeable fluorescent protein includes (a) a peptide linker region linked at either the amino or carboxyl end of the modified GFP, the linker region susceptible to digestion by a specific protease; and (b) a fluorescence modifier moiety linked to the end of the linker region so as to change the fluorescence characteristics of the modified GFP when linked to the protein. The modified protein can be used for cellular assays which are not dependent on GFP expression by the cell.

The invention is further directed to kits containing any one of the engineered fluorescent proteins described herein or polynucleotide sequences encoding them.

Unless otherwise defined, all technical and scientific terms used herein have the same meaning as commonly understood by one of ordinary skill in the art to which this invention belongs.

Other objects, advantages and features of the present invention will become apparent from the following specification taken in conjunction with the accompanying drawings.

BRIEF DESCRIPTION OF THE SEVERAL VIEWS OF THE DRAWINGS

FIG. 9 is the amino acid sequence alignment for native GFP and its differently colored variants: blue (BFP), yellow (YFP), and cyan (CFP).

FIG. 10 is the DNA sequence for E17R/D19R/D21R/E111R/E124R GFP.

DETAILED DESCRIPTION OF THE INVENTION

The present invention is broadly directed to novel engineered variants of fluorescent proteins, which are freely permeable to cells. Suitable variants were created by altering the charge profile of the residues on the exterior of a fluorescent protein molecule. By making at least one exterior surface of the protein cationic (positively charged profile), through site-directed mutagenesis, a fluorescent protein capable of cellular entry was generated. The ability of the engineered fluorescent proteins to permeate cells obviates the need for transfections. Thus, this is the first example of a cell permeable fluorescent protein that does not require an internalization tag. These proteins may be further modified for use in monitoring in vivo protease activity and for developing genetic constructs for more diverse biological applications.

Figure 1:
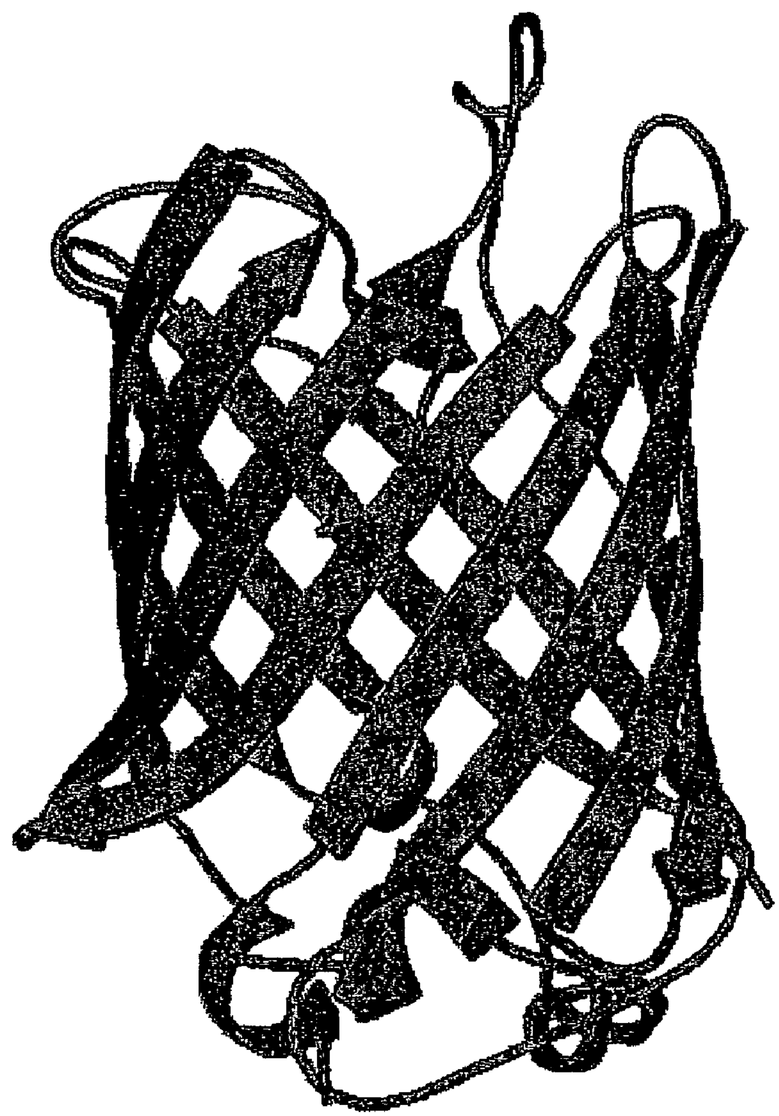
FIG. 1 is a representation of the tertiary structure of the native green fluorescent protein.

To achieve cell permeable fluorescent proteins, as a model, applicants chose to employ the GFP from the jellyfish *Aequorea victoria*, which has been cloned and the primary amino acid structure has been deduced (Prasher, D. C., et al., *Gene* 111:229-233 (1992) and FIG. 9 herein). Shown in FIG. 1 is a model for the tertiary structure of native GFP. The protein is formed as a stable cylindrical structure, the cylinder being formed of a series of beta sheets. The chromophore of GFP is positioned inside the cylindrical structure. The chromophore is a hexapeptide composed of amino acid residues 64-69 in which the amino acids at positions 64-67 form a heterocyclic ring. The protein is a very stable one, being thermostable over 70° C., but it does not enter into cells when placed in medium in which cells are cultured. GFP is a well-characterized acidic protein with a convenient signal for detecting cellular uptake—intrinsic fluorescence. (See, Zacharias, D. A. & Tsien, R. Y. *Methods Biochem. Anal.* 47, 83-120 (2006)).

Despite these advantages, however, the use of native or wildtype GFP has a few limitations. One example is the excitation and emission maxima of wildtype GFP are not within the range of wavelengths of standard fluorescence optics, resulting in low fluorescence intensity. To overcome this limitation applicants introduced selected point mutations into the native GFP sequence. More specifically, applicants made amino-acid substitutions in enhanced GFP (eGFP), which is the F64L/S65T variant and has desirable fluorescence properties. (See, Cormack, B. et al., *Gene* 173, 33-38 (1996), incorporated by reference here in its entirety).

The GFP protein, either native (SEQ ID NO: 1) or enhanced (SEQ ID NO: 5), was modified to a cationic state, the negatively charged residues on the protein were substituted with positively charged amino acid residues. The idea being to make substitutions to convert the charge profile of a face or patch of the exterior of the GFP protein from a mixed charge to a positive charge. The theory behind this concept is the majority of the saccharides on the exterior of most cells are negatively charged. Creating a positively charged face or patch on the exterior of the GFP protein will attract negatively charged saccharides on the cell exterior resulting in the cationic or cell permeable GFP being introduced into the cell.

Figure 2:
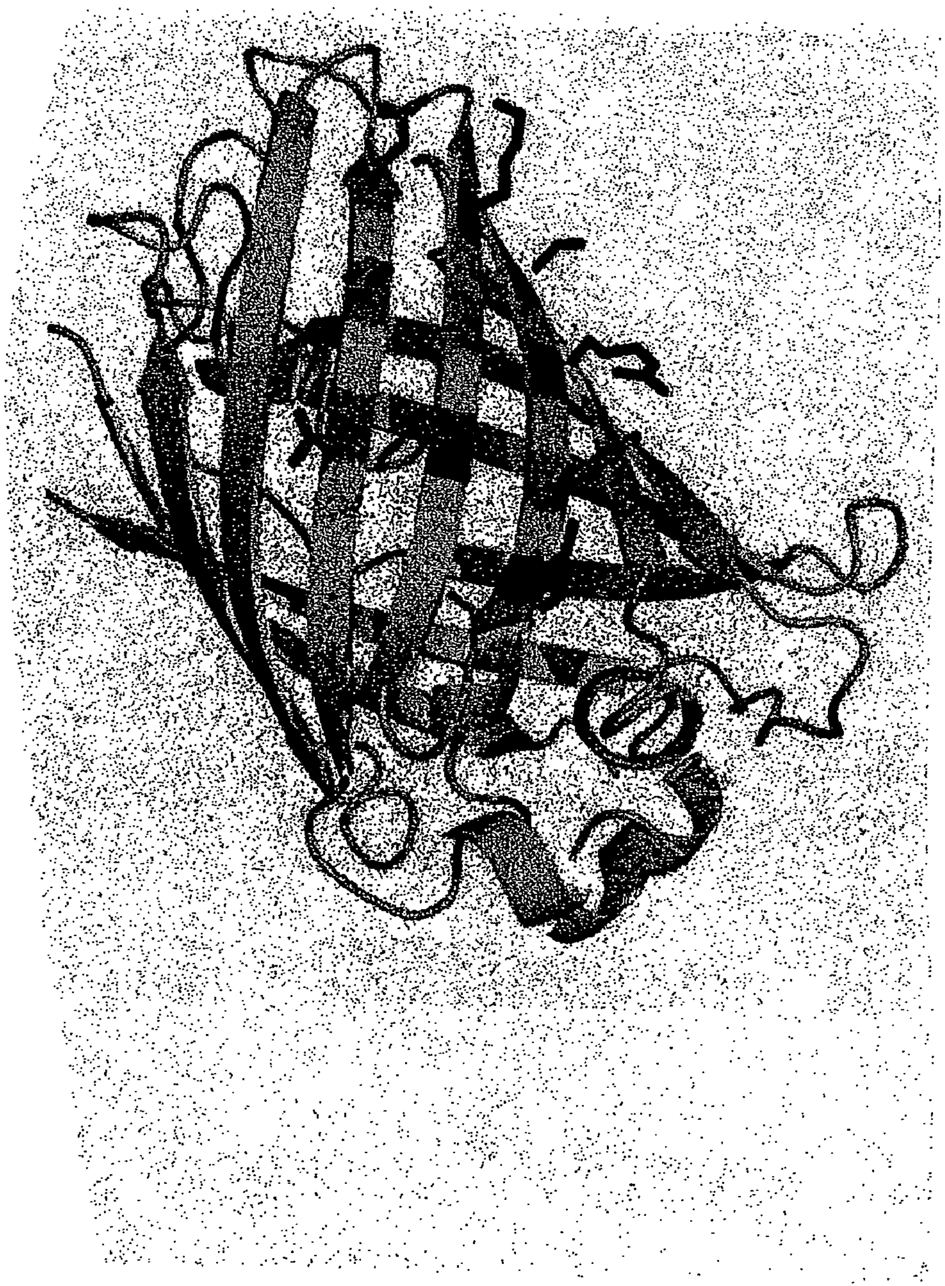
FIG. 2 is an illustration showing the location of charged residues on the exterior of the structure of the green fluorescent protein (GFP).

Shown in FIG. 2 is another view of the exterior of the GFP structure with one portion of the structure enlarged. In this view, the side chains of the amino acids of the protein are illustrated. The enlarged portion of the GFP surface is an area of mixed charge side chains in the native GFP protein. Indicated by the "+" sign are the side chains with positive charge and indicated with "−" sign are the side chains with negative charge.

The modifications of the native amino acid sequence exemplified below are to replace all of the residues with negatively charged side chains in this region of the protein with alternative residues with positively charged side chains. The effect of these substitutions is to make this large area of surface of the protein all positively charged, to make a face or region of the surface of the protein positively charged. The rationale being the glycoproteins and glycolipids common on cell surfaces are predominantly negatively charged, and the electric charge attraction would bind the modified (cell permeable) GFP to cell surfaces for eventual ingestion into the interior of the cells. Notably, no cofactors or substrates are required for fluorescence, thus, the protein may be used in a wide variety of organisms and cell types.

As used herein the terms "engineered", "variant", or "modified" refer to a protein that has been subjected to site-directed mutagenesis, such that at least one of the amino acid residues with negatively charged side chains in the cylindrical body portions (exterior of the protein) are substituted with amino acids having positively charged side chains. Suitable variant proteins include fluorescent proteins, preferably GFP. However, the site-directed mutagenesis approach described herein is not limited to GFP, but may encompass other colored fluorescent proteins such as, cyan, blue, and yellow.

This rational design of a cpGFP proved correct in practice as the cpGFP was internalized in the presence of cells. Indeed, after introducing the modified cpGFP into the cell culture medium, fluorescence characteristics of GFP could then be observed in the cells themselves. However, this same phenomenon did not occur in other cell lines which were deficient in glycoaminoglycans (GAGs), the negatively charged chains on the exterior of the cell surfaces.

Thus, broadly characterized, one embodiment of the invention is an engineered fluorescent protein, preferably GFP, having amino acids with negatively charged side chains substituted with amino acids having positively charged side chains on the exterior of the protein, rendering the protein cell permeable. It is noted that such substitutions can be made to the native GFP, enhanced GFP as described herein or GFP having combinations of other mutations which would not interfere with the positive charge profile of an engineered cpGFP.

More specifically, in another embodiment, the invention provides an engineered form of a fluorescent protein, preferably GFP, that has at least one native amino acid residue with a negatively charged side chain substituted by an amino acid residue having a positively charged side chains. Locations of amino acid substitutions include positions 17, 19, 21, 111, and 124. The modified GFP is cell permeable.

The substitutions to the enhanced GFP sequence described in the example below are substitutions of glutamic acid (E) and aspartic acid (D) substituted in each instance with an arginine (R) residue. Arginine has a positively charged side chain as opposed to the negative charges on glutamic acid and aspartic residues. The substitutions are indicated in the specification here by the common nomenclature such as E17R, which indicates that the glutamic acid residue normally present at residue 17 in the amino acid sequence is substituted by an arginine residue at that location. The other possible substitutions would include other positively charged amino acids, such as lysine, for these or other negatively charged residues.

As used herein the phrase "positively charged amino acids" includes naturally occurring or non-naturally occurring basic amino acids. Preferred amino acid residues include but are not limited to arginine (R), lysine (K) and histidine (H).

As used herein the phrase "negatively charged amino acids" includes naturally or non-naturally occurring acidic amino acids. Preferred amino acid residues include, but are not limited to glutamic acid (E) and aspartic acid (D).

Another embodiment of the invention includes an engineered fluorescent protein, preferably GFP, wherein the protein has E17R, D19R, D21R, E111R, and E124R substitutions. It should be noted these five amino acid substitutions described in the example below are sufficient to achieve cell permeability. It is contemplated that more such substitutions are possible to increase the permeability of the modified GFP to cells. These five substitutions are all in the cylindrical body portions of the GFP tertiary structure. Since this change to the protein sequence occurs far from the region of the chromophore of the protein, the change does not affect the fluorescent properties of the molecule in any way. Thus, these same substitutions will similarly affect on other modified forms of GFP where the modifications to the other forms are intended to affect the fluorescence characteristics of the protein.

In addition to conferring cell permeability to a native or an enhanced fluorescent proteins as described herein, it is contemplated that one could confer cell permeability to other modified proteins, preferably GFP, having a combination of mutations resulting in desirable properties. The properties could vary from higher expression in mammalian cells, higher fluorescence intensity under UV or white light illumination, etc. A number of other genetic modifications could be made to GFP resulting in variants for which spectral shifts correspond to changes in the cellular environment such as pH, ion flux, and the phosphorylation state of the cell which can be accomplished using standard techniques routine in the art. Thus, in addition to possessing such properties, the fluorescent protein may be endowed with a cationic "patch" (by making the exterior surface charge positive) giving the protein affinity for negatively charged GAGs on the cell surface.

Another embodiment includes methods for making the engineered GFPs. The method includes culturing host cells containing a nucleic acid molecule (an expression vector) encoding an engineered GFP alone or in tandem with other genes under conditions favoring the production of a cpGFP and isolating the cpGFP from the host cell. These engineered proteins can be produced using both eukaryotic and prokaryotic cells.

Unless otherwise specified, a nucleotide sequence encoding an amino acid sequence includes all nucleotide sequences that are degenerate versions of each other and that encode the same amino acid sequence.

In conjunction with production of the engineered proteins, specific plasmids, expression vectors, promoters, selection methods and host cells are disclosed and used herein and in the Examples, other promoters, vectors, selection methods and host cells, both prokaryotic and eukaryotic, are well-known to one of ordinary skill in the art and may be used to practice the present invention without departing from the scope of the invention or any of the embodiments thereof.

The cpGFP and modifications thereof will have utility as fluorescent tags and fluorescent enzyme substrates in living cells. For example, in the examples below, a small-molecule fluorescent quencher is attached to the cpGFP via a peptide tag that is cleavable by HIV protease. This molecule could be used to (1) screen for viruses, such as HIV in human cells and (2) separate infected cells which would have unquenched GFP fluorescence from uninfected cells with quenched GFP fluorescence.

Another embodiment of the invention includes a linker-modified cell permeable fluorescent protein employed to assay the presence of protease in cells. The linker-modified protein including (a) a modified GFP in which at least three of the negatively charged amino acid residues, preferably glutamic acid or aspartic acid, in the native or enhanced GFP are substituted by residues having positively charged side chains including arginine or lysine residues, the modified GFP being permeable; (b) a peptide linker region linked at either the amino or carboxyl end of the modified green fluorescent protein, the linker region susceptible to digestion by a specific protease; and (c) a fluorescence modifier moiety linked to the end of the linker region, the fluorescence modifier changing the fluorescence characteristics of the modified green fluorescent protein if linked to the protein, so the presence of the protease can be assayed in cells by placing the linker-modified cell permeable fluorescent protein in the presence of the cells. Both eukaryotic and prokaryotic cells are detectable using the engineered cell permeable fluorescent proteins. Suitably, host cell lines may include but are not limited to CHO, VERO, BHK, HeLa, COS, MDCK, Jurkat, HEK-293, and W138.

As used herein the term "linker region" refers to a peptide moiety. The preferred linker moiety is a peptide between about one and 30 amino acid residues in length, preferably between about two and 15 amino acid residues. In one example, the linker has the amino acid sequence TSFNFPQITC (SEQ ID NO: 13). The linker region is designed to be digestible by a specific protease, such as HIV-1 protease. Other peptide moieties recognized in the literature are within the scope of the invention.

Attached covalently to the carboxyl terminal of the linker is a "fluorescence modifier moiety". This moiety, suitably TMR (tetramethyl rhodamine) has the effect of modifying the fluorescence characteristics of GFP and other fluorescent proteins (YFP, BFP, CFP), if and only if the modifier is in close proximity to the GFP itself. If the TMR is in close proximity to the GFP, the fluorescence of the GFP is higher relative to the normal GFP where the TMR is in further proximity. Other fluorescence modifier moieties which may interact with GFP are also encompassed herein, such as, eosin, eosin Y or eosin B.

A related embodiment includes a method for assaying cells in culture for activity of specific protease, suitably HIV-1 protease. The method includes placing the linker-modified cell permeable GFP in culture with cells and then measuring the fluorescent characteristics of the cells, wherein a higher than normal fluorescence is indicative of protease present in the cells.

The materials of the invention are ideally suited for a kit to facilitate a variety of applications. In preferred embodiments the compositions (polynucleotides and polypeptides) of the invention may be assembled into kits for use in labeling target polypeptides with the present cpGFPs or in vivo monitoring of protease activity in a cell sample.

The subject kits generally include at least one container containing, for example, a cpGFP or a cpGFP having a peptide linker region and a fluorescence modifier moiety linked thereto as described herein (i.e., linker-modified cell permeable GFP). Preferably the kit may include any one of the engineered cpGFP proteins (SEQ ID NOs: 6 and 7) or polynucleotide sequences encoding these proteins (SEQ ID NOs: 8 and 9). In the subject kits, the above components may be combined into a single aqueous composition or separate as different or disparate compositions, e.g. in separate containers. Other reagents may be included in the kit.

In addition to the above components, the subject kits may further include instructions for practicing the subject methods. These instructions may be present in the kits in a variety of forms including but not limited to paper or computer readable form.

The following examples are provided as further non-limiting illustrations of compositions and methods for practicing the claimed embodiments.

EXAMPLES

Materials

The Plasmid pRSET$_B$, containing a cDNA for enhanced GFP (eGFP) which directs the production of a DNA for eGFP was obtained from Dr. S. James Remington (University of Oregon). Since the modifications to eGFP from the native sequence were to enhance fluorescence, the use of GFP rather than native GFP was considered equivalent. Oligonucleotides for site-directed mutagenesis of this DNA (eGFP cDNA) were obtained from Integrated DNA Technologies (Coralville, Iowa) and had the sequences: 5' CACTGGAGTTGTCCCAATTCTTGTTCGTTTACGTGGT CGTGTTAATGGGCACAAATTT TCTGTCAGTGG 3' (SEQ ID NO: 10 and its reverse complement; sites of the E17R, D19R, and D21R substitutions are underlined), 5' CGGGAACTACAAGACACGTGCT CGTGTCAAGTTTGAAGGTGATACCC 3' (SEQ ID NO: 11 and its reverse complement; the site of the E111R substitution is underlined), and 5' CCCTTGTTAATAGAATC CGTTTAAAAGGTATT GATTTTAAAG 3' (SEQ ID NO: 12 and its reverse complement; the site of the E124R substitution is underlined). DH5α and BL21(DE3) competent *Escherichia coli* cells were from Stratagene (La Jolla, Calif.).

Example 1

Site-Directed Mutagenesis

A variety of site-directed mutagenic techniques may be used to prepare the GFP mutants described here. Such methods are well known and standard in the literature. To practice the invention, plasmids that direct the production of eGFP variants were obtained from plasmid pRSETB by using the QuikChange mutagenesis kit (Stratagene, La Jolla, Calif.) with complementary oligonucleotides described above. Three successive rounds of mutagenesis yielded DNA encoding eGFP with five substitutions: E17R, D19R, D21R, E111R, and E124R. The engineered protein with at least three of these changes (i.e., E17R, D19R, and D21R) and preferably all five of these changes is referred to as "cationic GFP" or simply "cpGFP". The amino acid sequences of GFP and several of its differently colored variants are set forth in FIG. 9 attached below, which also shows the acidic residues mutated to arginine in the modified GFP disclosed above. FIG. 10 sets forth the nucleotide sequence of a coding region sufficient to express E71R, D19R, D21R, E111R/E124R cell permeable GFP (SEQ ID NO: 9).

Example 2

Protein Production

Plasmids containing the sequences for and directing the production of eGFP and its variants were transformed into BL21(DE3) cells and colonies were selected on Luria-Bertani (LB) agar plates by their resistance to ampicillin. Starter cultures (25 mL) of LB medium containing ampicillin (200 μg/mL) were inoculated with a single colony of *E. coli* and grown at 37° C. with shaking at 200 rpm to an optical density of 0.6 at 600 nm. Cultures (1.0 L) of the same medium were inoculated with 4 mL of the starter culture and grown at 37° C. with shaking at 300 rpm to an optical density of 0.6 at 600 nm. Cultures were then cooled to 15° C., and gene expression was induced by the addition of isopropyl β-D-1-thiogalactopyranoside (IPTG) (final concentration: 1 mM). Cultures were grown at 15° C. with shaking at 300 rpm for 18 hours, and cells were harvested by centrifugation (5,000 rpm for 10 min) in a Beckman Coulter Avant J-20 XPI centrifuge using a JLA 8.1 rotor. Cell pellets were either frozen or used immediately to purify protein.

Example 3

Protein Purification

Cell pellets were resuspended in 10 mL of ice-cold cell lysis buffer, which was 50 mM sodium phosphate buffer (pH 7.2) containing 500 mM NaCl (500 nM) and PMSF (1 mM). Cells were lysed by sonication (50% duty/50% output) five times for 30 seconds. Cell debris was removed by centrifugation at 22,000×g for 60 minutes at 4° C. in a Beckman Optima XL-80K ultracentrifuge using a 60 Ti rotor. Clarified cell lysate was dialyzed for at least 2 hours against PBS+, which was 50 mM sodium phosphate buffer (pH 7.2) containing NaCl (636 mM) before loading onto a column of Ni-NTA agarose resin (Qiagen, Germany). The resin was washed with the same buffer containing 20 mM imidazole before eluting with 50 mM sodium phosphate buffer (pH 7.2) containing NaCl (636 mM) and imidazole (500 mM). The fractions containing green-colored protein (that is, cGFP) were pooled and diluted 1/10 with water to lower the salt concentration. The cGFP was then loaded onto a 5-mL column of HiTrap SP FF sepharose resin (Amersham Biosciences, Piscataway, N.J.). Protein was eluted with a 100-mL linear gradient (50 mL+50 mL) of NaCl (0-1.00 M) in 50 mM sodium phosphate buffer (pH 7.2).

Fractions containing green-colored protein were pooled and dialyzed against 50 mM sodium phosphate buffer (pH 7.5) containing NaCl (636 mM). The N-terminal histidine tag was removed as described previously (Hanson et al. *J. Bio.*

*Chem.,* 279, 13044-13053 (2004)). Briefly, protein was incubated with α-chymotrypsin (1:50 w/w) for 20 hours at room temperature. Chymotrypsin degrades the N-terminal tag but does not cleave the GFP protein (Hanson et al. 2004). Protein was concentrated with Vivascience 5000 MW spin columns, and protein concentration was determined by optical absorbance at 280 nm ($\epsilon_{280}$=19890 $M^{-1}cm^{-1}$) or by the BioRad protein assay.

Example 4

Cell Internalization

Chinese hamster ovary cells (CHO-K1), glycosaminoglycan-deficient cell lines (CHO-677 and CHO-745) and HeLa cells were obtained from the American Type Culture Collection (ATCC) and maintained according to recommended instructions. The day before incubation with a protein, cells were seeded onto 4- or 8-well Lab-Tek II Chambered Coverglass tissue culture dishes (Nalge Nunc International, Naperville, Ill.) to yield 75% confluency the next day. The following day, protein solutions (in PBS+500 mM NaCl) were added to cells in 200 μL (volume of the protein solution was <1/20 of the total volume) of medium or PBS containing magnesium (1 mM) and calcium (1 mM). Protein was incubated with cells for the indicated time. The cells were then washed three times with PBS containing magnesium and calcium prior to visualization. In some experiments, cell nuclei were counterstained with Hoescht 33342 for 5 minutes prior to washing with PBS. Internalization was visualized on a Nikon C1 laser scanning confocal microscope equipped with 60× and 100× lenses. The cpFGP is capable of crossing cell membranes rapidly and can be visualized by fluorescence microscopy in the cytoplasm of cultured human cells in under one hour.

Example 5

Conformational Stability

The conformational stability of GFP variants was determined by following the change in fluorescence as a function of denaturant concentration (Stepanenko, O. V. et al. *Biochemistry* 43, 14913-14923 (2004)). GFP proteins (1-5 nM) were incubated in 96-well flat-bottom plates (total volume: 100 μL) in 50 mM sodium phosphate buffer, pH 7.5, containing NaCl (500 mM) and guanidine-hydrochloride (Gdn-HCl) (0-6.30 M) for 24 h at room temperature. Fluorescence intensity was determined using a Tecan Ultra 384 fluorescence plate reader. Data were fitted to a two-state unfolding mechanism and could be used to calculate the standard free energy of denaturation: delta G° (=−RT ln K), where R is the gas constant, T is the absolute temperature, and K is the equilibrium constant calculated from the experimental data with the equation (see Tanford, C. *Adv. Protein Chem.* 23, 121-282 (1968): $K=[y_N-y]/[y-y_D]$. The value of y is the observed fluorescence value, and $y_N$ and $y_D$ are the y values for the native and denatured states, respectively.

Example 6

Fluorescent Properties

Fluorescence measurements were made with a QuantaMaster 1 photon counting fluorometer equipped with sample stirring (Photon Technology International, South Brunswick, N.J.). Fluorescence excitation and emission spectra were obtained in PBS+buffer using a 2-nm slit width and 1-nm/second scanning rate. Quantum yield (Φ) was determined following a method described previously (Cubitt et al. *Methods Cell Biol.,* 58, 19-30 (1999)). Briefly, the ultraviolet absorbance at 490 nm of cGFP in PBS+was matched to that of a fluorescein standard in 0.1 N NaOH of known quantum yield ($\Phi_f$=0.95 in 0.1 N NaOH). The area under the emission spectra from 500-700 nm (excitation at 490 nm) was determined, and the ratio (cGFP area/fluorescein area) was used to calculate the quantum yield of cGFP (cGFP area/fluorescein area=Φ cGFP/Φ fluorescein).

Example 7

Electrostatic Potential Diagrams

Electrostatic potential diagrams were made by using the atomic coordinates for F64L/S65T/Y66L GFP (Protein Data Bank entry 1S6Z4, see Rosenow, M. A., Biochemistry 43, 4464-4472 (2004)) and the program MacPyMol (DeLano Scientific, South San Francisco, Calif.). Default settings were used except that the Coulomb dielectric was set to be 80. A model of cpGFP was created and likewise modeled by using the program MacPyMol.

Example 8

Preparation of Linker-Modified Cell Permeable Fluorescent Proteins

The Plasmid pRSETB, containing a cDNA for enhanced GFP (eGFP) which directs the production of a DNA for eGFP was obtained. As indicated above, since the modifications to eGFP from the native sequence were to enhance fluorescence, the use of GFP rather than native GFP was considered equivalent. Oligonucleotides for site-directed mutagenesis of this DNA (eGFP cDNA) were obtained from Integrated DNA Technologies (Coralville, Iowa) and had the sequences: 5' GGCATGGATGAACTATACAAAACGG TGTCGTTCAATTTCCCGCAGATCACGTGTTAATAAGGATCCGAGCTCGAGATCTG 3' (SEQ ID NO: 14) and reverse complement where the HIV-PR cleavage site is underlined (corresponding to TVSFNFPQITC (SEQ ID NO: 15)). The primers to delete residues 230-238 of eGFP had the following sequence: 5' GAGTTTGTAACAGCTGCTGGGATTACGGTGTCGTTCAATTTCCCG 3' (SEQ ID NO: 16) and reverse complement. DH5α and BL21(DE3) competent *Escherichia coli* cells were from Stratagene (La Jolla, Calif.). The primers to make the mutations C48S and C70V respectively were 5' CCAATTGCTACCAGAGCAAGTCCACCATGAGAATCACCG 3' (SEQ ID NO: 17) and 5' CTCTCACTTATGGTGTTCAAGTCTTTTCAAGATACCCAG 3' (SEQ ID NO: 18) with respective complements. DH5α and BL21(DE3) competent cells were from Stratagene (La Jolla, Calif.).

One potential application for cpGFPs is as cell permeable substrates for cellular enzymes. In this case, cpGFP would be fused to another fluorescent molecule, such as a fluorophore or another fluorescent protein, through an amino acid linker. To prepare the linker-modified GFP variant described here, plasmids that direct the production of eGFP variants were obtained from plasmid pRSETB by using the QuikChange mutagenesis kit (Stratagene, La Jolla, Calif.) with complementary oligonucleotides described above. These oligonucleotides encode for a linker sequence that corresponds to a naturally occurring cleavage site for HIV-1 protease. However, this amino acid linker can be replaced with any amino acid sequence of length 2 to 20 amino acids that may or may not encode for a variety of other protein recognition sequences. In the example where cpGFP would be fused to a small molecule, this linker would also contain the amino acid cysteine, that could react with thiol-reactive small molecules. In this case, it may be necessary to make substitutions to the naturally occurring cysteine residues within GFP at positions 48 and 70 to ensure site-specific modification of the cysteine in the aforementioned linker sequence. The native cysteine residues in GFP at positions 48 and 70 may be replaced with serine and valine using site-directed mutagenesis and the primers listed above. These substitutions do not interfere with the fluorescent or cell permeable properties of cpGFP.

To produce the linker-modified GFP mutants, plasmids containing the sequences for and directing the production of eGFP and its variants were transformed into BL21 (DE3) cells. Colonies were selected and the cells were cultured as described above. The IPTG-induced cells were harvested and the cell pellets were either frozen or used immediately to purify the engineered protein. To purify the linker-modified cpGFP proteins cell pellets were subjected to the same purification protocol as described above for other engineered fluorescent proteins. The purified linker-modified cell permeable fluorescent proteins may be used for a variety of in vitro and in vivo applications.

Discussion

Figure 3:
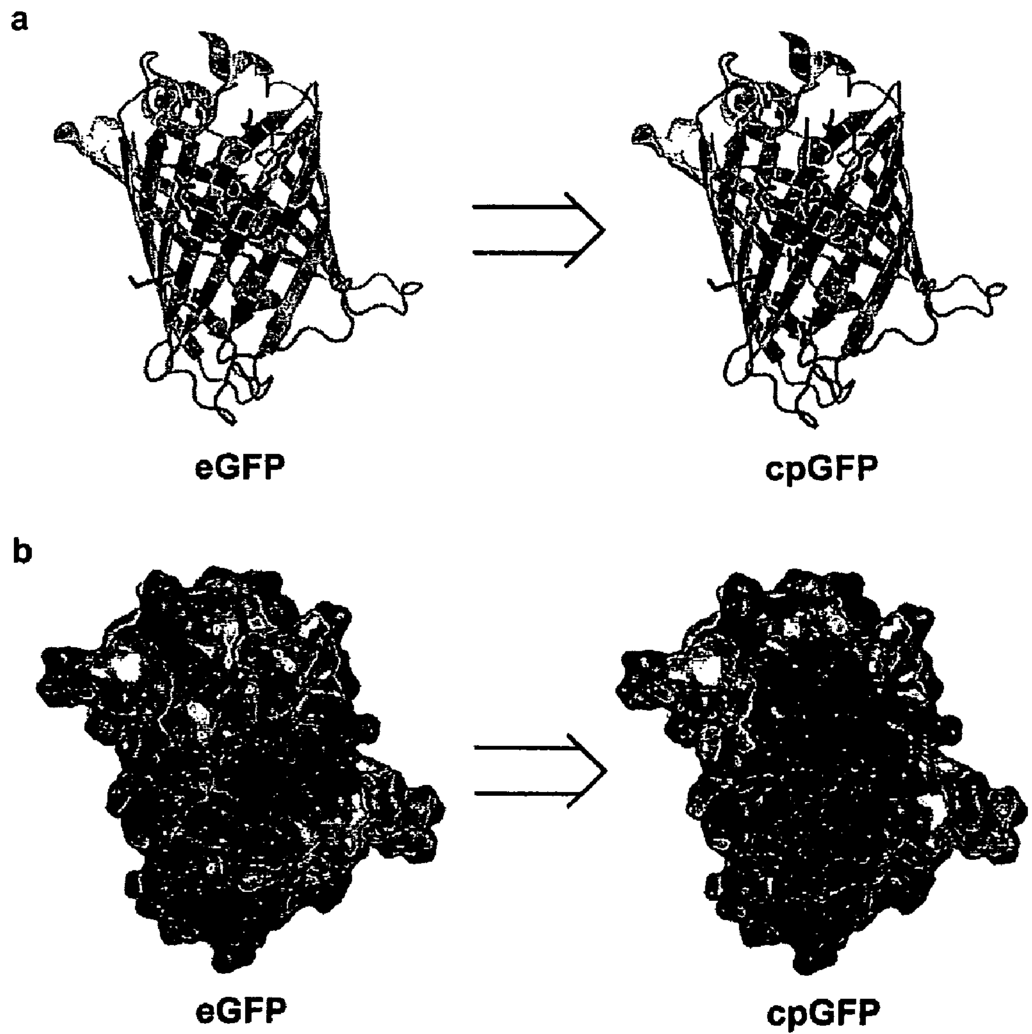
FIGS. 3A-B show the design of a cationic or cell-permeable variant of GFP (cpGFP).

GFP is an acidic protein, having a net charge (i.e., Arg+Lys−Asp−Glu) of Z=−9 at neutral pH. Applicants noted that one face of GFP is variegated with acidic and basic residues (FIG. 3A). Shown in FIG. 3A is a ribbon model depicting the location of the five anionic residues in GFP that were replaced with arginine to yield a surface comprised of ten cationic residues. The fluorophore is depicted in space-filling mode. Applicants chose to replace the five acidic residues (Glu17, Asp19, Asp21, Glu111, and Glu124) on this face with arginine. These acidic residues reside on three, adjacent Beta-strands, proximal to five basic residues (Lys107, Arg109, Lys113, Lys122, and Lys126). Accordingly, these five substitutions created a highly cationic patch on the surface of eGFP yielding a nearly neutral (Z=+1) variant that applicants refer to as cell-permeable GFP (cpGFP) seen FIG. 3*b*). FIG. 3B shows a space-filling model depicting the effect of the arginine substitutions on the electropotential surface (blue: cationic; red: anionic).

Figure 4:
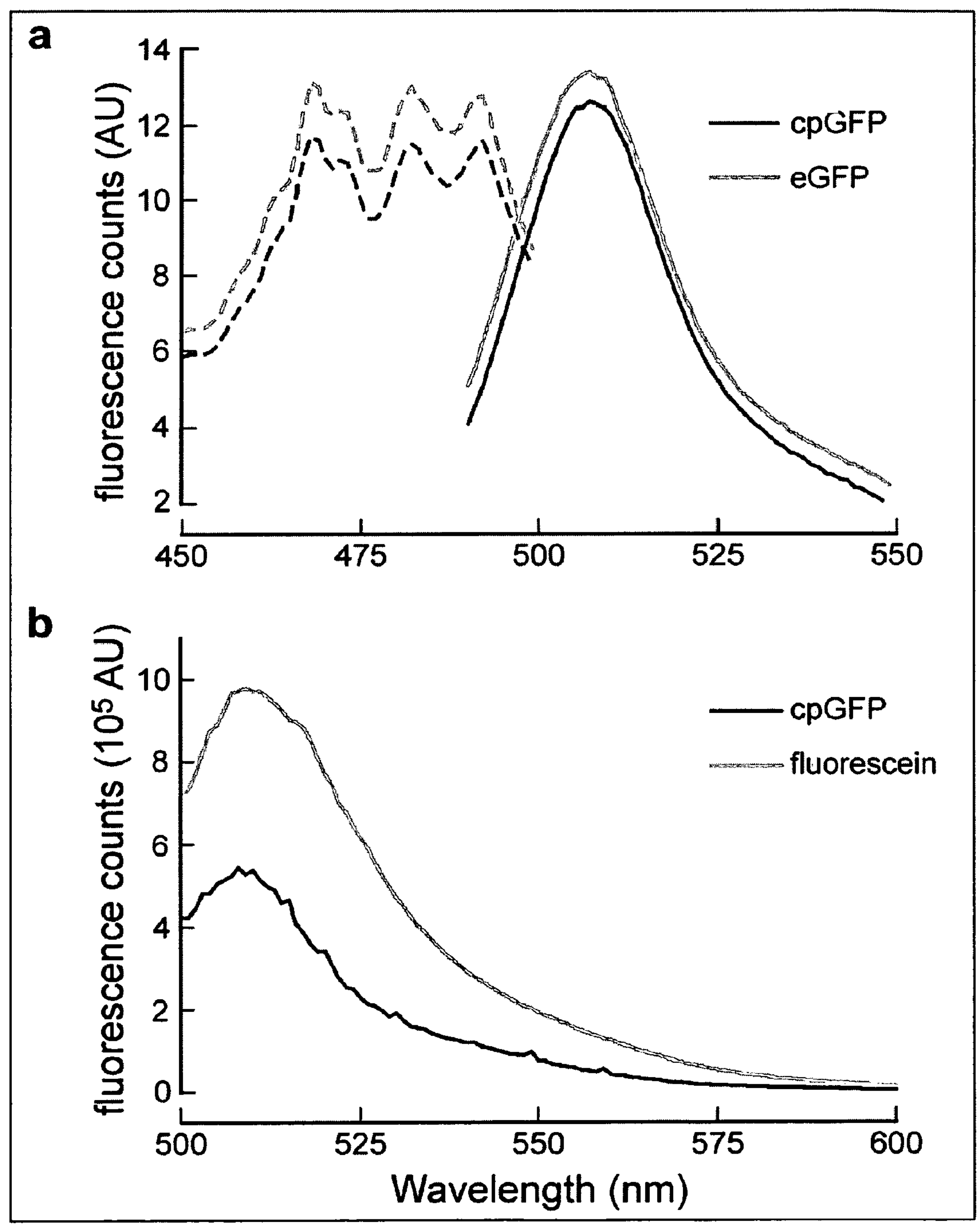
FIGS. 4A-B show fluorescence properties of cpGFP.

Applicants produced cpGFP in *Escherichia coli*. (See, Hanson, G. T. et al. *Biochemistry* 41, 15477-15488 (2002)). Cation-exchange chromatography was especially efficacious in the purification of cpGFP, affording nearly homogeneous protein. The fluorescence properties of cpGFP were found to be nearly identical to those of eGFP (see FIG. 4). Specifically, FIGS. 4A-B show fluorescence properties of cpGFP. (a) Fluorescence excitation (----) and emission (-) spectra for cpGFP (blue) and eGFP (green). Data were collected in 1-nm increments with a scan rate of 5 nm/s. (b) Raw data for determination of the quantum yield (Φ) for cpGFP. Solutions of cpGFP (blue) and fluorescein (green) (Φ fluorescein=0.95 in 0.10 N NaOH) of equal absorbance at 490 nm were diluted in PBS+ (for cpGFP) or 0.10 N NaOH (for fluorescein), and the area under the emission spectrum curves from 500-700 nm was determined. The quantum yield of cpGFP was determined with the equation: Φ cpGFP=Φ fluorescein(cpGFP area/fluorescein area).

Figure 5:
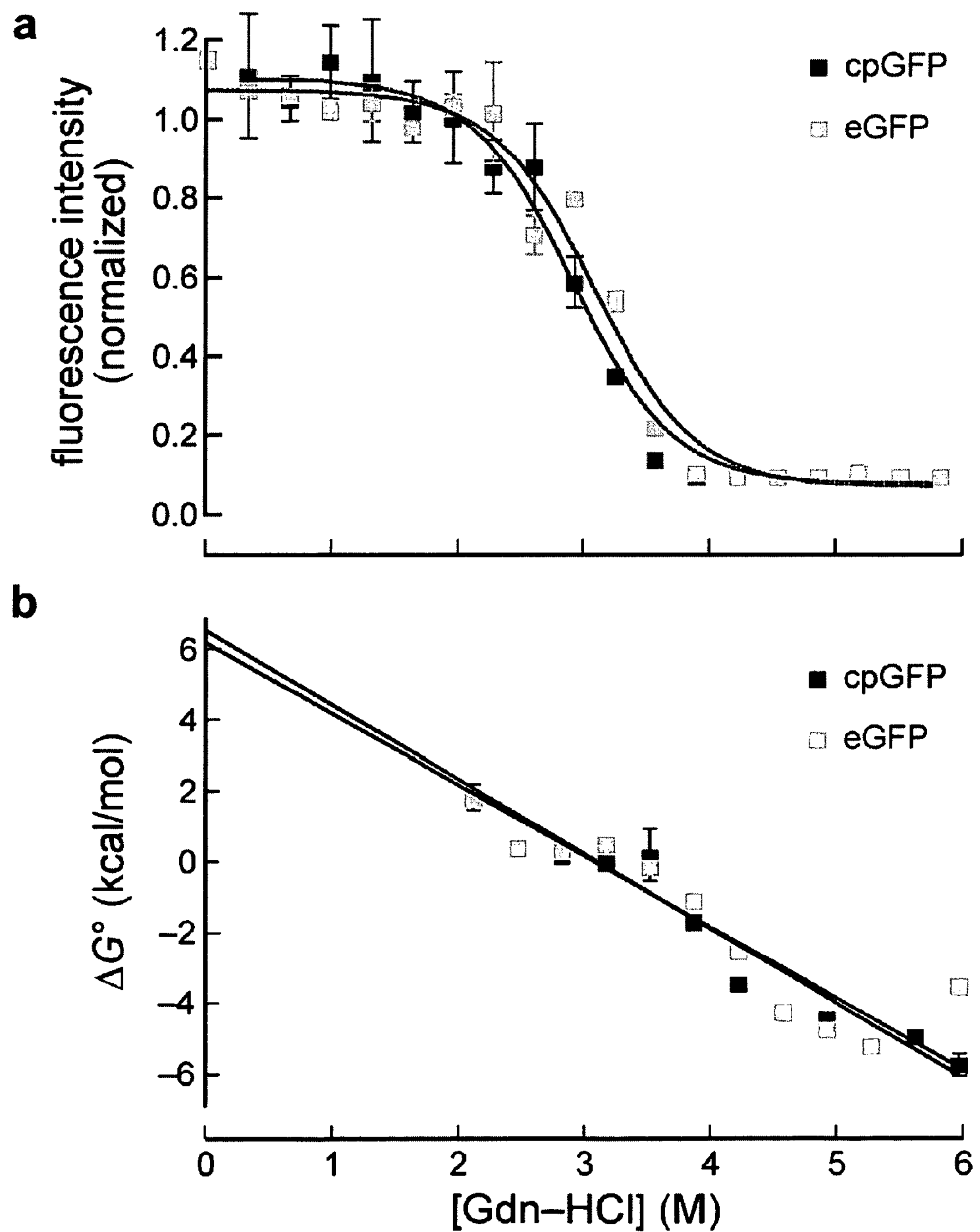
FIGS. 5A-B show conformational stability of cpGFP.

Formation of the GFP fluorophore requires its proper folding. (See Cody, C. et al., *Biochemistry* 32, 1212-1218 (1993); and Waldo, G. et al., *Nat. Biotechnol.* 17, 691-695 (1999)). Moreover, use of GFP requires the retention of its conformational stability in biological assays. Replacing anionic residues with cationic ones can alter protein stability, though this effect is not readily predictable. (See, Pace, C. et al., *Protein Sci.* 9, 1395-1398 (2000)). Hence, applicants used chemical denaturation to ascertain the effect of site-specific cationization on the stability of eGFP. Applicants observed that both cpGFP and eGFP have unfolding midpoints at $C_{1/2}$=(3.1±0.3) M guanidine-HCl (see FIG. 5). Specifically, FIGS. 5A-B show conformational stability of cpGFP. The unfolding of cpGFP (blue) and eGFP (green) were induced by Gdn-HCl. (a) Dependence of normalized fluorescence intensity on denaturant concentration. The midpoint of the transformation was fitted to a sigmoidal dose-response curve with the program Prism (Graphpad Software, San Diego, Calif.). The midpoint of the transition corresponds to the value of $C_{1/2}$, which is the concentration of denaturant at which the protein is 50% unfolded at equilibrium. (b) Dependence of $\Delta G^o$ on Gdn-HCl concentration. Data were fitted to a bilinear regression such that the slope (m) is the dependence of $\Delta G^o$ on denaturant and the y-intercept approximates the free energy of the protein in the absence of denaturant ($\Delta G^o \sim \Delta G(H2O)$). Thus, the creation of a cationic patch did not have a deleterious effect on conformational stability.

Cellular internalization of GFP can be visualized by fluorescence microscopy. Applicants incubated cells with increasing concentrations of either cpGFP or eGFP for known times at 37° C. Prior to visualization, cells were placed in fresh medium for 1 h to allow for the internalization of any protein bound to the cell surface. Specifically, HeLa cells were incubated with cpGFP (a, 10 μM; b, 1 μM; c, 0.1 μM) and eGFP (d, 10 μM) for 3 h in Opti-MEM medium at 37° C. Cells were then placed in fresh medium for 1 h and stained with Hoescht 3342 (blue) and propidium iodide (red) for 15 min prior to visualization by confocal microscopy. Fluorescence intensity within living cells was dose-dependent, increasing at high concentration of cpGFP (FIG. 6*a-c*). Although a small amount was detectable in the cytosol, cpGFP was observed primarily in vesicles. This localization is similar to that observed with cationic peptides, such as polyarginine. (See, Fuchs, S. M. & Raines, R. T. *Biochemistry* 43, 2438-2444 (2004)). Insignificant fluorescence intensity was observed in cells incubated with eGFP (FIG. 6*d*).

Glycosaminoglycans (GAGs) such as heparan sulfate (HS) and chondroitin sulfate (CS) on the cell surface can mediate the binding of cationic peptides and proteins. (See, Fuchs, S. M. & Raines, R. T. *Cell. Mol. Life. Sci.* 76, 1819-1822 (2006); Fuchs, S. M. & Raines, R. T. *Biochemistry* 43, 2438-2444 (2004); and Richard, J. P. et al. *J. Biol. Chem.* 280, 15300-15306 (2005)). To probe for a role for GAGs in cpGFP internalization, applicants compared cell-surface binding and cellular internalization of cpGFP in wild-type CHO-K1 cells to that in a CHO cell line that is deficient in GAG biosynthesis. Specifically, CHO-K1 and CHO-745 cells (which are GAG-deficient) were incubated with cpGFP (2 μM) for 3 h at 37° C. in Opti-MEM medium. Cells were then placed in fresh medium for 1 h and stained with Hoescht 33342 (blue) and propidium iodide (red) for 15 min prior to visualization.

Figure 6:
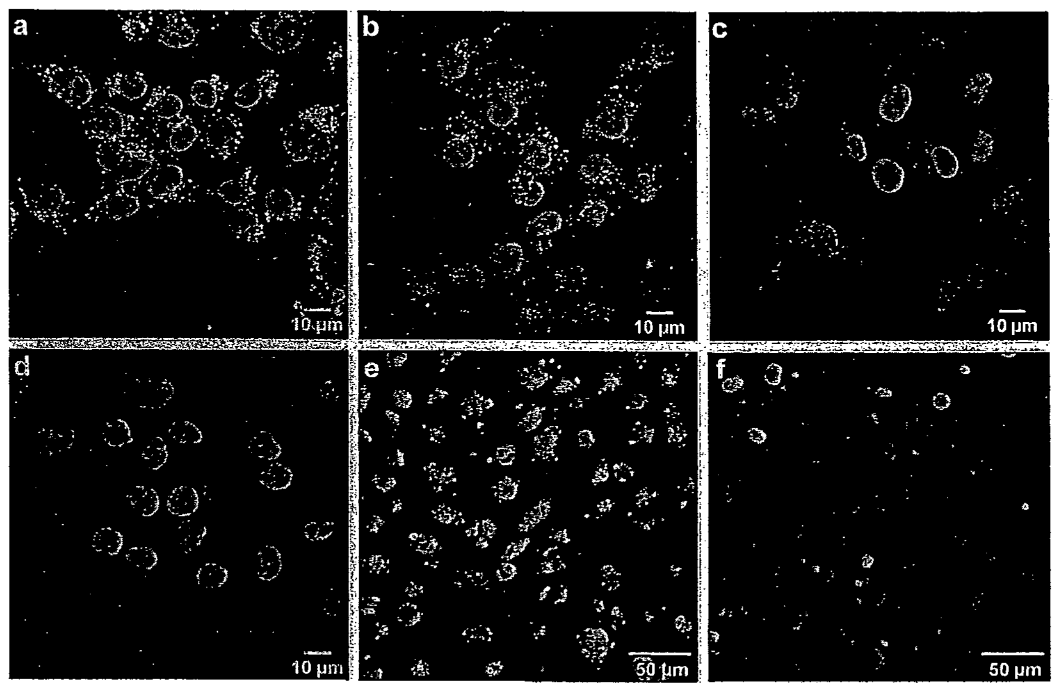
FIGS. 6A-F show images of the internalization of cpGFP variants into living cells.
Figure 7:
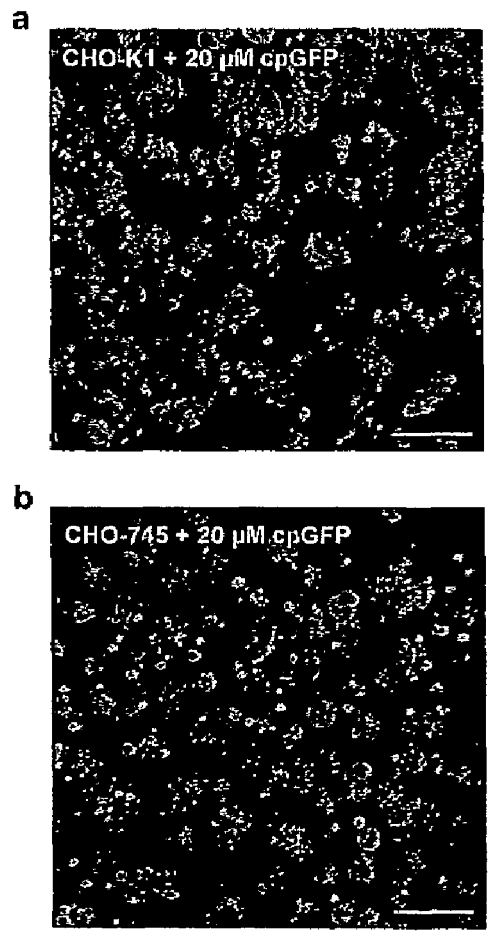
FIGS. 7A-B show cellular internalization of cpGFP in CHO-K1 and CHO-745 cells at high concentration.

In wild-type CHO-K1 cells, cpGFP was observed to bind to the cell surface and undergo internalization (FIG. 6*e*). In CHO-745 cells (which are deficient in HS and CS), there is little internalization of cpGFP (FIG. 6*f*). At a 10-fold higher protein concentration, cpGFP is internalized in the GAG-deficient cell line (see FIG. 7). Specifically, FIGS. 7A-B show cellular internalization of cpGFP in CHO-K1 and CHO-745 cells at high concentration. cpGFP (20 μM) was added to Opti-MEM medium containing CHO-K1 (a) and CHO-745 (b) cells, and incubated for 3 h at 37° C. Cells were then placed in fresh medium for 1 h, and stained with Hoescht 33342 (blue) prior to visualization. Scale bars: 50 μm. Similar results were obtained with another GAG-deficient cell line, CHO-677 (data not shown). Apparently, cpGFP internalization relies largely, but not exclusively, on the interaction with cell surface GAGs.

GFP and its variants are in widespread use in cell biology. (See, Zacharias, D. A. & Tsien, R. Y. *Methods Biochem. Anal.* 47, 83-120 (2006); and Ward, T. H. & Lippincott-Schwartz, *J. Methods Biochem. Anal.* 47, 305-337 (2006)). Among these variants, cpGFP is unique in obviating a need for transfection to infuse mammalian cells with a fluorescent protein, and thus could have numerous applications, both in vitro and in vivo. (See, Hoffman, R. M. *Nat. Rev. Cancer* 5, 796-806 (2005)). More generally, our data demonstrate that an exogenous chain of arginine residues (which is readily susceptible to proteolysis) is not a necessary component of a cell-permeable protein. (See, Fuchs, S. M. & Raines, R. T. *Protein Sci.* 14, 1538-1544 (2005)). Applicants anticipate that site specific cationization will be a useful means to endow proteins other than GFP with cell permeability.

Figure 8:
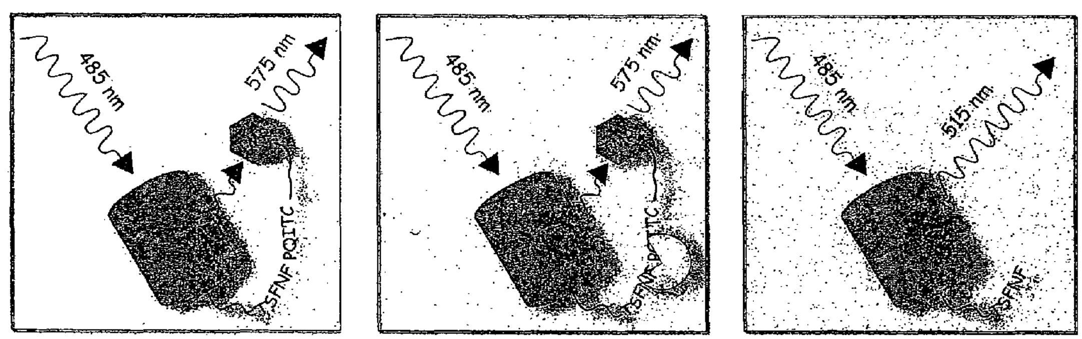
FIG. 8 is an illustration of a variant of the present invention showing a cell permeable GFP with a selectively degradable linked region and a fluorescence modifying moiety attached thereto.

Furthermore, a unique application of the cell permeable GFP is illustrated in FIG. 8. FIG. 8 shows a linker-modified cell permeable GFP. This embodiment of the engineered GFP has attached to it a linker region, specifically a peptide as set forth in sequence TSFNFPQITC (SEQ ID NO: 13). This peptide linker region is designed to be digestible by a specific protease, in this case the HIV-1 protease. Attached covalently to the carboxyl terminal of the linker is a molecule designed as TMR (tetramethyl rhodamine) which has the effect of modifying the fluorescence characteristics of GFP if and only if the modifier is in close proximity to the GFP itself. If the TMR is in close proximity to the GFP, the fluorescence of the GFP is at 575 nm, as opposed to the normal fluorescence at 515 nm characteristic of enhanced GFP. In this usage, close proximity means close enough to alter the fluorescence characteristics of the GFP.

The linker-modified cell permeable fluorescent protein can be introduced into the medium in which cells are cultured, resulting in the protein entering the cell. If the cells into which the GFP permeated contain HIV-1 protease, the protease will digest the linker and the GFP in those cells will fluoresce at 515 nm in those cells. If the cells contain no HIV-1 protease, the linker will not be digested and the GFP in those cells will fluoresce at 575 nm. Thus a simple fluorescent assay for expression of HIV-1 protease is enabled. This assay can be used to test or sort individual cells or can be used to test or assay a cell culture or cell sample from a host. This same methodology may be used to provide an assay for the expression of any protease of interest in any cell type or cell source.

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

All publications and patents mentioned in the above specification are herein incorporated by reference. Various modifications and variations of the described method and system of the invention will be apparent to those skilled in the art without departing from the scope and spirit of the invention. It is understood, however, that examples and embodiments of the present invention set forth above are illustrative and not intended to confine the invention. The invention embraces all modified forms of the examples and embodiments as come within the scope of the following claims.

We claim:

1. An engineered fluorescent protein comprising a fluorescent protein differing in amino acid sequence from the reference protein of SEQ ID NO: 1-3 or 5, wherein the difference consists of an amino acid residue having a positively charged side chain substituted in at least one of the residues at positions 17, 19, 21, 111, and/or 124 of SEQ ID NO:1-3 or 5, and wherein the engineered fluorescent protein is rendered permeable to cells in culture.

2. The engineered fluorescent protein as claimed in claim 1, wherein the fluorescent protein differing from the reference protein of SEQ ID NO: 1-3 or 5 has E17R, D19R, D21R, E111R, and E124R substitutions.

3. A kit comprising any one of the engineered fluorescent proteins as claimed in claim 1.

4. An engineered fluorescent protein comprising a fluorescent protein differing in amino acid sequence from the reference protein of SEQ ID NO: 1-3 or 5, wherein the difference consists of an amino acid residue having a positively charged side chain substituted at positions 17, 19, and 21 of SEQ ID NO:1-3 or 5, and wherein the engineered fluorescent protein is rendered permeable to cells in culture.

5. A kit comprising the engineered fluorescent protein as claimed in claim 4.

6. An engineered fluorescent protein comprising a fluorescent protein differing in amino acid sequence from the reference protein of SEQ ID NO: 1-3 or 5, wherein the difference consists of an amino acid residue having a positively charged side chain substituted in at least three of the residues at positions 17, 19, 21, 111, and 124 of SEQ ID NO:1-3 or 5, and wherein the engineered fluorescent protein is rendered permeable to cells in culture.

7. An engineered fluorescent protein comprising a fluorescent protein differing in amino acid sequence from the reference protein of SEQ ID NO: 1-3 or 5, wherein the difference consists of substituting a glutamic acid or a aspartic acid with an arginine or a lysine at positions 17, 19, and 21 of SEQ ID NO:1-3 or 5, and wherein the engineered fluorescent protein is rendered permeable to cells in culture.

8. The engineered fluorescent protein as claimed in claim 7, wherein the fluorescent protein differing from the reference protein of SEQ ID NO: 1-3 or 5 has E17R, D19R, and D21R substitutions.

9. An engineered fluorescent protein comprising a fluorescent protein differing in amino acid sequence from the reference protein of SEQ ID NO: 4, wherein the difference consists of an amino acid residue having a positively charged side chain substituted in at least one of the residues at positions 18, 20, 22, 112, and/or 125 of SEQ ID NO: 4, and wherein the engineered fluorescent protein is rendered permeable to cells in culture.

10. The engineered fluorescent protein as claimed in claim 9, wherein the fluorescent protein differing from the reference protein of SEQ ID NO: 4 has E18R, D20R, D22R, E112R, and E 125 R substitutions.

11. A kit comprising any one of the engineered fluorescent proteins as claimed in claim 9.

12. An engineered fluorescent protein comprising a fluorescent protein differing in amino acid sequence from the reference protein of SEQ ID NO: 4, wherein the difference consists of substituting a glutamic acid or an aspartic acid with an arginine or a lysine at positions 18, 20, and 22 of SEQ ID NO: 4, and wherein the engineered fluorescent protein is rendered permeable to cells in culture.

13. The engineered fluorescent protein as claimed in claim 12, wherein the fluorescent protein differing from the reference protein of SEQ ID NO: 4 has E18R, D20R, and D22R substitutions.

* * * * *

SEQUENCE LISTING

```
<160> NUMBER OF SEQ ID NOS: 18

<210> SEQ ID NO 1
<211> LENGTH: 238
<212> TYPE: PRT
<213> ORGANISM: Aequorea victoria

<400> SEQUENCE: 1

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Thr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
```

-continued

```
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 2
<211> LENGTH: 238
<212> TYPE: PRT
<213> ORGANISM: Aequorea victoria

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Thr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 3
<211> LENGTH: 238
<212> TYPE: PRT
<213> ORGANISM: Aequorea victoria
```

-continued

```
<400> SEQUENCE: 3

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Thr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser Gly Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 4
<211> LENGTH: 239
<212> TYPE: PRT
<213> ORGANISM: Aequorea victoria

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Thr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

-continued

```
Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 5
<211> LENGTH: 238
<212> TYPE: PRT
<213> ORGANISM: Artificial
<220> FEATURE:
<223> OTHER INFORMATION: Synthetic protein

<400> SEQUENCE: 5

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Thr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 6
<211> LENGTH: 238
```

<212> TYPE: PRT
<213> ORGANISM: Artificial
<220> FEATURE:
<223> OTHER INFORMATION: Synthetic protein

<400> SEQUENCE: 6

```
Met Ser Lys Gly Glu Glu Leu Phe Thr Gly Val Val Pro Ile Leu Val
1               5                   10                  15

Arg Leu Arg Gly Arg Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Thr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 7
<211> LENGTH: 238
<212> TYPE: PRT
<213> ORGANISM: Artificial
<220> FEATURE:
<223> OTHER INFORMATION: Synthetic protein

<400> SEQUENCE: 7

```
Met Ser Lys Gly Glu Glu Leu Phe Thr Gly Val Val Pro Ile Leu Val
1               5                   10                  15

Arg Leu Arg Gly Arg Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Thr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95
```

-continued

```
Thr Ile Phe Phe Lys Asp Asp Gly Asn Tyr Lys Thr Arg Ala Arg Val
            100                 105                 110

Lys Phe Glu Gly Asp Thr Leu Val Asn Arg Ile Arg Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

```
<210> SEQ ID NO 8
<211> LENGTH: 828
<212> TYPE: DNA
<213> ORGANISM: Artificial
<220> FEATURE:
<223> OTHER INFORMATION: Synthetic polynucleotide

<400> SEQUENCE: 8

atgcggggtt ctcatcatca tcatcatcat ggtatggcta gcatgactgg tggacagcaa      60

atgggtcggg atctgtacga cgatgacgat aaggatcccc ccgctgaatt catgagtaaa     120

ggagaagaac ttttcactgg agttgtccca attcttgttc gtttacgtgg tcgtgttaat     180

gggcacaaat tttctgtcag tggagagggt gaaggtgatg caacatacgg aaaacttacc     240

cttaaattta tttccactac tggaaaacta cctgttccat ggccaacact tgtcactact     300

ctcacttatg gtgttcaatg cttttcaaga tacccagatc atatgaaacg gcatgacttt     360

ttcaagagtg ccatgcccga aggttatgta caggaaagaa ctatattttt caaagatgac     420

gggaactaca agacagaagc tcgtgtcaag tttgaaggtg atacccttgt taatagaatc     480

gaattaaaag gtattgattt taaagaagat ggaaacattc ttggacacaa attggaatac     540

aactataact cacacaatgt atacatcatg gcagacaaac aaaagaatgg aatcaaagtt     600

aacttcaaaa ttagacacaa cattgaagat ggaagcgttc aactagcaga ccattatcaa     660

caaaatactc caattggcga tggccctgtc cttttaccag acaaccatta cctgtccaca     720

caatctgccc tttcgaaaga tcccaacgaa aagagagacc acatggtcct tcttgagttt     780

gtaacagctg ctgggattac acatggcatg gatgaactat acaaataa                  828

<210> SEQ ID NO 9
<211> LENGTH: 828
<212> TYPE: DNA
<213> ORGANISM: Artificial
<220> FEATURE:
<223> OTHER INFORMATION: Synthetic polynucleotide

<400> SEQUENCE: 9

atgcggggtt ctcatcatca tcatcatcat ggtatggcta gcatgactgg tggacagcaa      60

atgggtcggg atctgtacga cgatgacgat aaggatcccc ccgctgaatt catgagtaaa     120
```

-continued

```
ggagaagaac ttttcactgg agttgtccca attcttgttc gtttacgtgg tcgtgttaat    180

gggcacaaat tttctgtcag tggagagggt gaaggtgatg caacatacgg aaaacttacc    240

cttaaattta tttccactac tggaaaacta cctgttccat ggccaacact tgtcactact    300

ctcacttatg gtgttcaatg cttttcaaga tacccagatc atatgaaacg gcatgacttt    360

ttcaagagtg ccatgcccga aggttatgta caggaaagaa ctatattttt caaagatgac    420

gggaactaca agacacgtgc tcgtgtcaag tttgaaggtg atacccttgt taatagaatc    480

cgtttaaaag gtattgattt taaagaagat ggaaacattc ttggacacaa attggaatac    540

aactataact cacacaatgt atacatcatg gcagacaaac aaaagaatgg aatcaaagtt    600

aacttcaaaa ttagacacaa cattgaagat ggaagcgttc aactagcaga ccattatcaa    660

caaaatactc caattggcga tggccctgtc cttttaccag acaaccatta cctgtccaca    720

caatctgccc tttcgaaaga tcccaacgaa aagagagacc acatggtcct tcttgagttt    780

gtaacagctg ctgggattac acatggcatg gatgaactat acaaataa                828
```

```
<210> SEQ ID NO 10
<211> LENGTH: 69
<212> TYPE: DNA
<213> ORGANISM: Artificial
<220> FEATURE:
<223> OTHER INFORMATION: Synthetic polynucleotide

<400> SEQUENCE: 10

cactggagtt gtcccaattc ttgttcgttt acgtggtcgt gttaatgggc acaaattttc     60

tgtcagtgg                                                             69


<210> SEQ ID NO 11
<211> LENGTH: 47
<212> TYPE: DNA
<213> ORGANISM: Artificial
<220> FEATURE:
<223> OTHER INFORMATION: Synthetic polynucleotide

<400> SEQUENCE: 11

cgggaactac aagacacgtg ctcgtgtcaa gtttgaaggt gataccc                   47


<210> SEQ ID NO 12
<211> LENGTH: 42
<212> TYPE: DNA
<213> ORGANISM: Artificial
<220> FEATURE:
<223> OTHER INFORMATION: Synthetic polynucleotide

<400> SEQUENCE: 12

cccttgttaa tagaatccgt ttaaaaggta ttgattttaa ag                        42


<210> SEQ ID NO 13
<211> LENGTH: 10
<212> TYPE: PRT
<213> ORGANISM: Artificial
<220> FEATURE:
<223> OTHER INFORMATION: Synthetic peptide

<400> SEQUENCE: 13

Thr Ser Phe Asn Phe Pro Gln Ile Thr Cys
1               5                   10


<210> SEQ ID NO 14
<211> LENGTH: 80
```

-continued

```
<212> TYPE: DNA
<213> ORGANISM: Artificial
<220> FEATURE:
<223> OTHER INFORMATION: Synthetic polynucleotide

<400> SEQUENCE: 14

ggcatggatg aactatacaa aacggtgtcg ttcaatttcc cgcagatcac gtgttaataa     60

ggatccgagc tcgagatctg                                                 80


<210> SEQ ID NO 15
<211> LENGTH: 11
<212> TYPE: PRT
<213> ORGANISM: Artificial
<220> FEATURE:
<223> OTHER INFORMATION: Synthetic peptide

<400> SEQUENCE: 15

Thr Val Ser Phe Asn Phe Pro Gln Ile Thr Cys
1               5                   10


<210> SEQ ID NO 16
<211> LENGTH: 45
<212> TYPE: DNA
<213> ORGANISM: Artificial
<220> FEATURE:
<223> OTHER INFORMATION: Synthetic polynucleotide

<400> SEQUENCE: 16

gagtttgtaa cagctgctgg gattacggtg tcgttcaatt tcccg                     45


<210> SEQ ID NO 17
<211> LENGTH: 39
<212> TYPE: DNA
<213> ORGANISM: Artificial
<220> FEATURE:
<223> OTHER INFORMATION: Synthetic polynucleotide

<400> SEQUENCE: 17

ccaattgcta ccagagcaag tccaccatga gaatcaccg                            39


<210> SEQ ID NO 18
<211> LENGTH: 39
<212> TYPE: DNA
<213> ORGANISM: Artificial
<220> FEATURE:
<223> OTHER INFORMATION: Synthetic polynucleotide

<400> SEQUENCE: 18

ctctcactta tggtgttcaa gtcttttcaa gatacccag                            39
```